United States Patent [19]

Ensslin

[11] Patent Number: 5,167,658
[45] Date of Patent: Dec. 1, 1992

[54] METHOD AND APPARATUS FOR ELECTROSURGICAL MEASUREMENT

[75] Inventor: Frieder H. Ensslin, Rochester, N.Y.
[73] Assignee: MDT Corporation, Torrance, Calif.
[21] Appl. No.: 648,207
[22] Filed: Jan. 31, 1991
[51] Int. Cl.⁵ .............................................. A16B 17/39
[52] U.S. Cl. .......................................... 606/34; 606/38
[58] Field of Search ........................ 606/34, 35, 37–40

[56] References Cited

U.S. PATENT DOCUMENTS

| | | | |
|---|---|---|---|
| 3,897,787 | 8/1975 | Ikuno et al. | 606/35 |
| 4,658,819 | 4/1987 | Harris et al. | 606/38 X |
| 4,727,874 | 3/1988 | Bowers et al. | 606/37 |

Primary Examiner—Lee S. Cohen
Attorney, Agent, or Firm—Trask, Britt & Rossa

[57] ABSTRACT

An improved method and apparatus for measuring the total energy delivered to a patient during an electrosurgical procedure. An electrosurgical target (the patient) is positioned atop a dispersive plate constituting a first electrode. The patient is included in the circuit comprising an electrosurgical generator, the plate electrode and a surgical instrument constituting a second electrode. A mathematical relationship between the current in the circuit and the load impedance is established for selected power settings of said generator. Current in the circuit is measured during electrosurgery by suitable means such as a current transformer. A computing device such as a microprocessor determines the impedence according to the relationship between current and impedence for the particular generator power setting being used. The microprocessor then computes the power delivered to the patient from the current and impedance values. The delivered power is integrated over time to determine the total energy delivered to the patient. The microprocessor may be further programmed to shut off the generator when a selected maximum total energy is delivered.

8 Claims, 3 Drawing Sheets

METHOD AND APPARATUS FOR ELECTROSURGICAL MEASUREMENT

BACKGROUND OF THE INVENTION

1. Field

This invention relates to electrosurgical apparatus and methods, such as those typified by devices marketed under the trademark "BOVIE ®" by MDT Corporation of Torrance, Calif. It is particularly directed to an improved method for determining the amount of energy dispensed during electrosurgical procedures into a patient.

2. State of the Art

Electrosurgical procedures, as generally practiced, involve the placement of a patient upon a large surface area electrode, commonly referred to as a dispersive plate. The plate electrode constitutes a first electrode associated with an electrosurgical generator. An electrosurgical instrument, which constitutes a second electrode associated with the electrosurgical generator is utilized to perform surgical procedures on the anatomy of a patient. As the instrument makes contact with the patient's body, energy is dispensed into the patient by virtue of the electrical circuit comprised of the dispersive plate electrode, the patient, the surgical instrument, and the electrosurgical generator. The rate at which energy is dispensed into the patient is conventionally defined as power.

Common electrosurgical procedures involve the cutting, abrading, vaporizing or cauterizing of the patient's tissues. As a consequence, significant amounts of energy are dispensed to the patient's body. For reasons of patient safety, and consistent with conservative surgical procedures generally, it is desirable for a surgical team to be able to estimate with reasonable accuracy the amount of electrical energy dispensed into a patient over discrete intervals of time involved in the surgical procedures. It is particularly important for the surgical team to monitor the total energy dispensed into the patient's body during the entire procedure from start to finish. Unfortunately, available electrosurgical devices provide no reliable basis from which accurate determinations of energy dispensed into a patient can be derived.

The control panels of electrosurgical generators typically include a power setting which indicates a percentage of maximum operating power. That is, the generator may be set at 100 percent, 50 percent, or some other selected value. That setting value is not precisely indicative of the actual rate (e.g., watts) at which power is delivered to the patient, however, because that value is dependent upon factors which affect the actual power deliverable at any time by the generator. Most notable among these is the highly variable impedance value contributed by the patient to the circuit. The power output of an electrosurgical generator is a function of load impedance, including the dominant contribution of the patient. Patient impedance varies considerably during a procedure as well as from patient to patient. Although certain available electrosurgical generators display a power value which reflects increased or decreased current flow, the power value displayed is computed from periodic current measurements made into a known, fixed impedance. The fixed impedance value does not correspond to the actual impedance in the circuit. Accordingly, the power value displayed may actually be misleading to the surgical team. To the extent the power value for a given procedure is made a matter of record, it is largely valueless and non-reproducible. Without accurate real time measurements of power (watts), it is not possible to obtain an accurate integrated quantity (e.g. watt hours) reflective of the total energy dispensed to a patient during an elapsed time.

For meaningful record keeping, and assistance in the repeatability of a procedure, for patient's safety, and for purposes of meaningful research involving patient energy tolerances or related matters, there remains a need for a method whereby the quantity of energy dispensed to a patient or research target in an electrosurgical procedure may be reliably measured.

SUMMARY OF THE INVENTION

According to the present invention, current readings are taken from the circuit which includes the patient plate, the electrosurgical instrument being used upon the patient, and the electrosurgical generator, during an electrosurgical procedure. Ideally, these readings are taken continuously, but the invention is operable with frequent readings. It is feasible to determine for any electrosurgical generator a mathematical relationship between current and impedance at any power level of interest. Such a relationship may be established empirically at any given power setting, e.g. 100 percent or 50 percent, by applying current to a load of known but variable impedance and recording the resulting current. The data may be plotted or reduced to a mathematical expression.

In any event, a current reading at any instant may be relied upon in accordance with the mathematical relationship characteristic of the generator at its selected power setting to determine the actual load impedance in the circuit. The measured current value and the determined load impedance value may be used to calculate the power, that is, the rate at which energy is being delivered to the patient, at that instant. With repeated or continuous current measurements and corresponding power calculations, power may be integrated over time from the commencement of the procedure to yield the total amount of energy dispensed to the patient or other target during the procedure up to the point of the last measurement.

The current readings are preferably inputted through an analog to digital converter into a computer programmed to derive the impedance value of the circuit and to calculate power. The computer may also integrate the power reading over time and drive auxiliary devices which either terminate power after a predetermined amount of total energy has been dispensed to the patient, display the power delivery in a preferred format, or make permanent records from which the procedure may be duplicated. Because relatively little processing or computing power or memory is required for any of these calculations or functions, most embodiments of the invention can be accommodated by a standard, readily available microprocessor installed within the electrosurgical generator housing.

BRIEF DESCRIPTION OF THE DRAWINGS

In the drawings, which illustrate what is presently regarded as the best mode for carrying out the invention.

DESCRIPTION OF THE ILLUSTRATED EMBODIMENT

Figure 1:
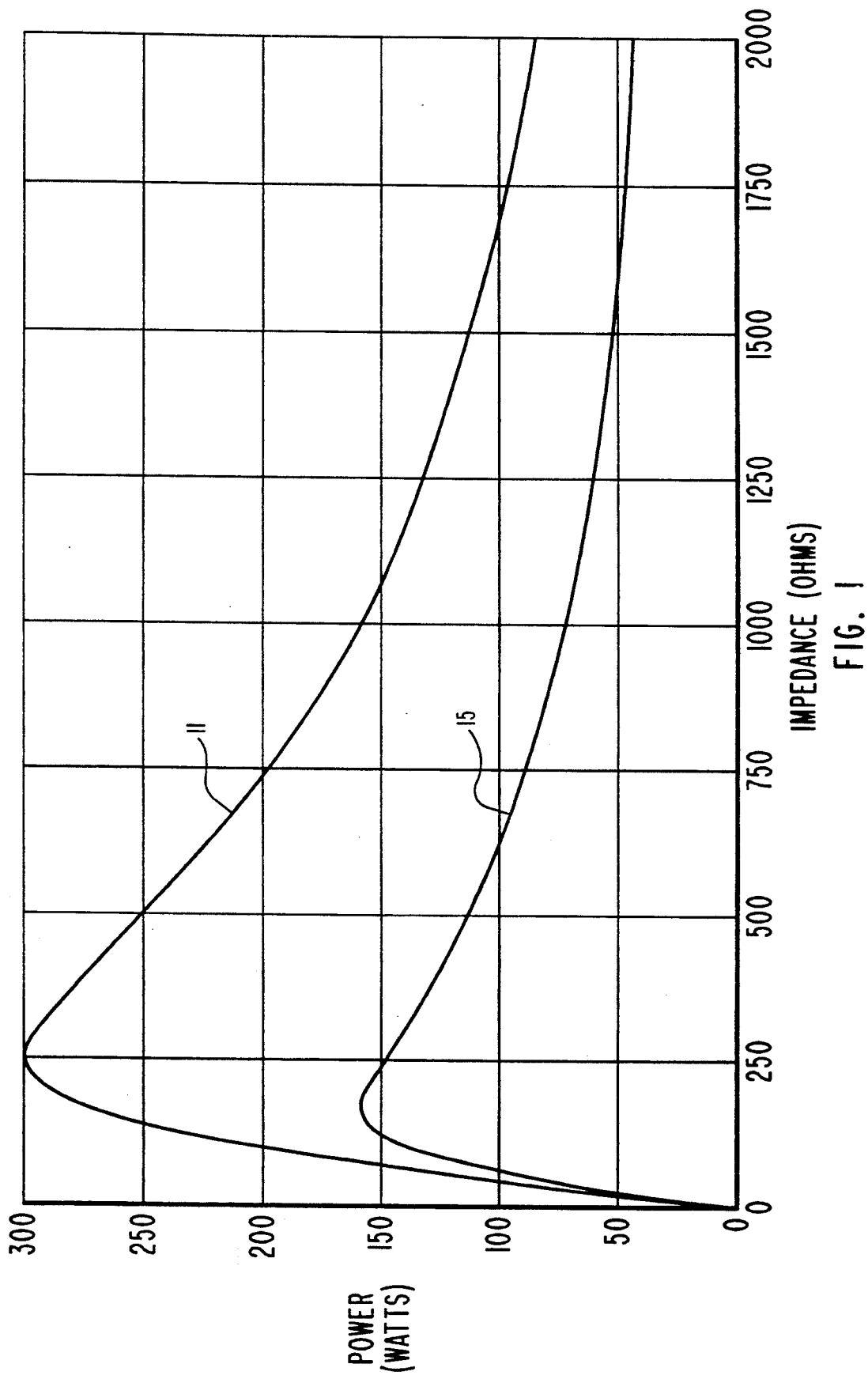
FIG. 1 is a plot of deliverable power in watts versus impedance in ohms representative of a typical electrosurgical generator set at 100 percent and 50 percent of maximum power, respectively.

Referring to FIG. 1, the curve 11 plots the cutting power in watts delivered by a typical electrosurgical generator set at its maximum power setting against impedance. Similar power curves are either published or derivable empirically for all available electrosurgical generators. The curve 15 is a similar plot with the same generator set at its 50 percent power setting. From a comparison of the curves 11 and 15 it is apparent that the power delivered to an instrument at the 50 percent power setting is generally less than half of the delivered power at the maximum power setting. An explanation for this disparity is that the internal resistance of the generator changes as the power setting is changed. Accordingly, for purposes of this invention, it is preferred that a power curve descriptive of the actual power setting of interest be determined.

Figure 2:
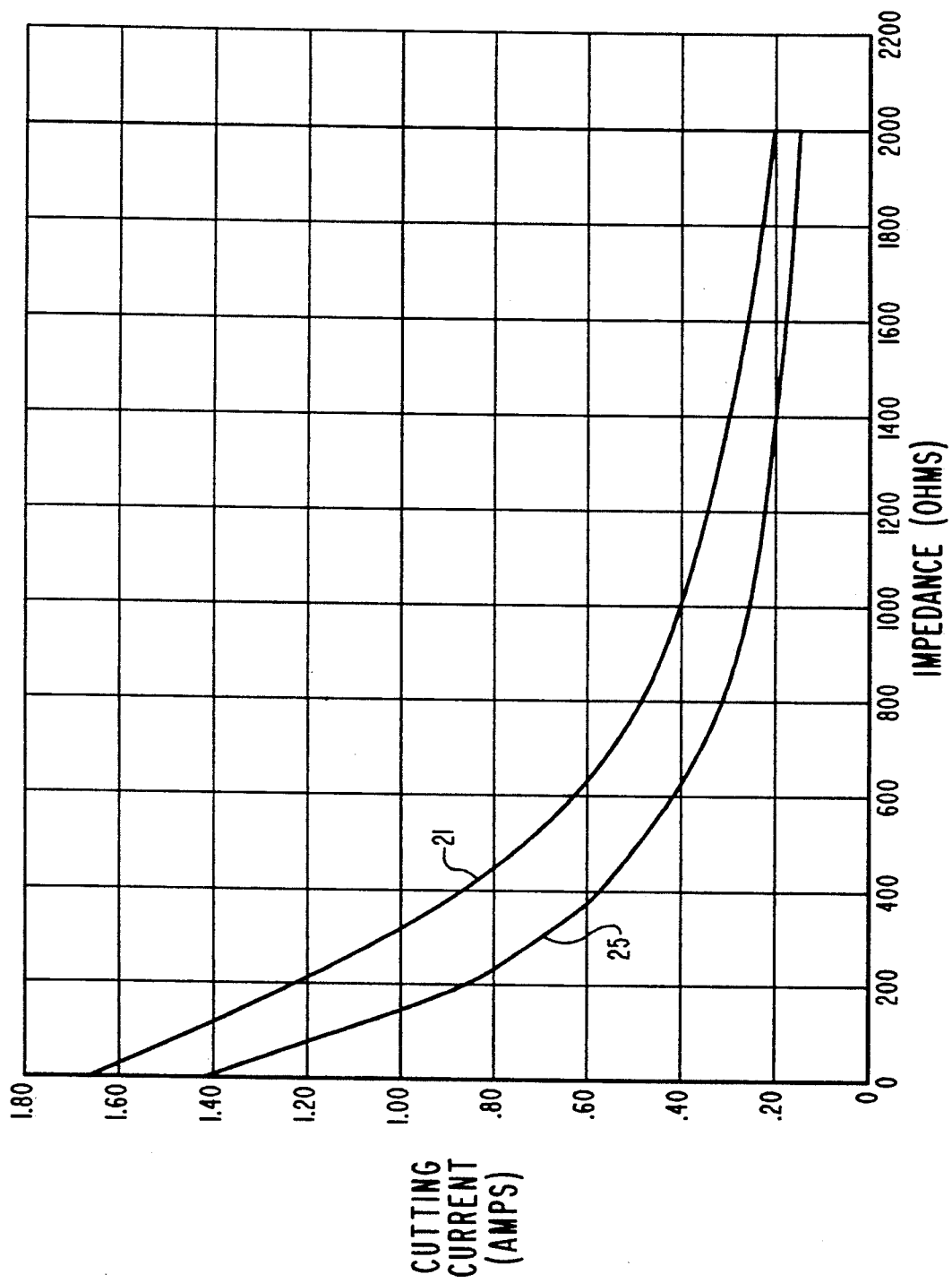
FIG. 2 is a plot of cutting current in amperes as a function of impedance for the electrical generator of FIG. 1.

The plots 21 and 25 of FIG. 2 correspond to the plots 11 and 15 of FIG. 1 and illustrate the mathematical relationship between cutting current and impedance for the same surgical generator described by FIG. 1. These curves may also be derived empirically for every power setting of interest.

The terms "cutting power" and "cutting current" should be understood to refer to the deliverable output power of the generator. Many surgical functions in addition to cutting are conventionally practiced in electrosurgery, and this invention finds application and utility in connection with many such procedures.

Figure 3:
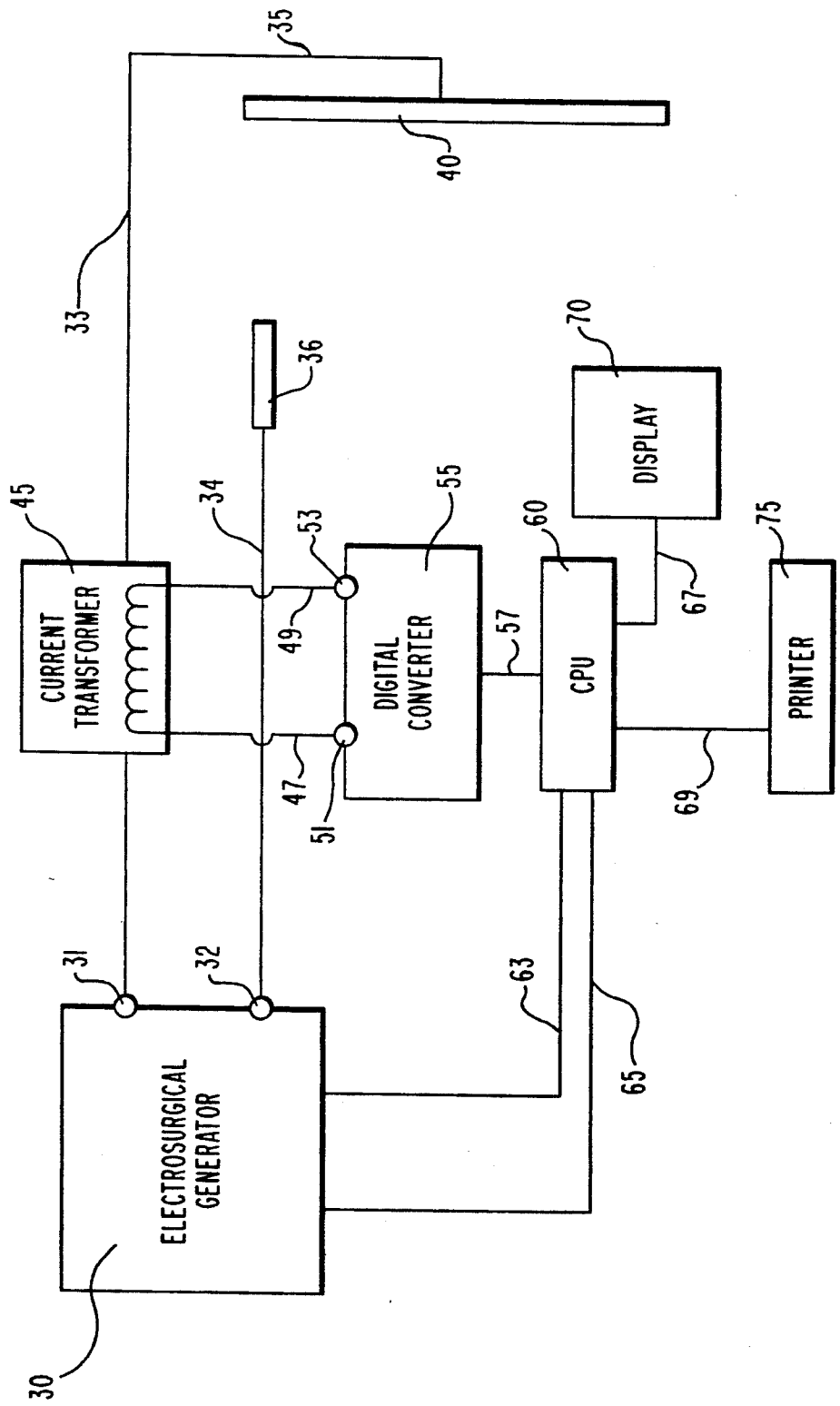
FIG. 3 is a block diagram illustrating the invention in association with a typical electrosurgical circuit.

FIG. 3 illustrates a typical system utilized for electrosurgical procedures but modified by the inclusion of components useful for the practice of this invention. An electrosurgical generator 30 has terminals 31, 32 to which are connected a dispersive patient plate 35 and an electrosurgical instrument 36, respectively. An electrosurgical target 40, which may be a patient, is shown in contact with the dispersive plate 35. When the surgical instrument 36 comes into contact with the target 40, an electrical circuit comprising the surgical instrument electrode 36, the target 40, the dispersive plate electrode 35 and the electrosurgical generator 30 is effected. Conductors 33 and 34 extend from terminals 31 and 32, respectively, to connect the dispersive plate electrode 35 and the surgical instrument electrode 36 as shown.

Current flowing through the circuit is detected at conductor 33 by means of a current transformer device 45, the leads 47, 49 of which are connected to the terminals 51, 53, respectively, of an analog to digital converter device 55. An output 57 from the converter 55 is fed to a central processing unit 60. The central processing unit 60 is connected by an input cable 63 and an output cable 65 to the electrosurgical generator 30. Output lines 67 and 69 are similarly connected to a display device 70 and a printer 75, respectively.

The central processing unit 60 (referred to hereinafter as a "CPU") is programmed to recognize the power setting (percent maximum power) of the generator 30, and to determine the actual load impedance of the circuit from the detected current value by reference to the mathematical relationship between current and impedance characteristic of the generator 30 at that power setting. A family of such relationships, as illustrated by FIG. 2, may be stored in memory. The CPU is further programmed to calculate the power delivered to the surgical target from the detected current value and the derived impedance value, such calculations being well-known in the art. Any or all of the electrical quantities detected, derived, or calculated may be stored in memory or forwarded to one or more display devices 70 or a printer 75. It is ordinarily desirable for the CPU to perform the calculations in real time. It is then feasible for the CPU to control the electrosurgical generator in response to detected current, calculated power, total energy dispensed, or any combination of these parameters. For example, it may sometimes be desirable for the generator 30 to be automatically shut down in response to signals from the CPU indicating that a predetermined amount of energy has been dispensed to the target 40 either over a prescribed increment of time or since the commencement of a procedure.

Reference herein to specific features of the illustrated embodiment is not intended to limit the scope of the appended claims which themselves recite those details regarded as important to the invention

What is claimed:

1. In an electrosurgical procedure of the type in which a target is positioned atop a dispersive plate constituting a first electrode associated with an electrosurgical generator, and a surgical instrument constituting a second electrode associated with said generator is applied to the target, thereby delivering energy into said target, an improved method for determining the amount of energy so delivered, said improvement comprising:
    establishing a mathematical relationship between current and load impedance at selected power settings of said generator;
    measuring the current in a circuit including said dispersive plate, said target, said electrosurgical instrument, and said generator during said electrosurgical procedure;
    determining from individual measurements of said current the corresponding load impedances according to said mathematical relationship;
    calculating from said individual measurements of current and said individual determinations of load impedances, power values corresponding to the power delivered to said patient at the times of said individual measurements; and
    integrating said power calculations over time, thereby to monitor the total energy delivered to said target over a period of time.

2. An improvement according to claim 1 wherein said individual measurements of current are converted to individual digital inputs to a computing device programmed to determine said corresponding load impedances in real time and to calculate said corresponding power values.

3. An improvement according to claim 2 wherein said current in said circuit is measured by means of a current transformer.

4. An improvement according to claim 2 wherein said computing device is programmed to turn off said generator when said total energy delivered to said target reaches a preselected amount.

5. An electrosurgical apparatus including:
    an electrosurgical generator;

conductors extending from terminals associated with said generator;

a pair of electrodes, each connected to one of said conductors and adapted to form a circuit including said generator, said conductors, and said electrodes, one of said electrodes being configured to contact an electrosurgical target and to include said electrosurgical target in said circuit;

a current transformer operably associated with one of said conductors to measure current flowing in said circuit; and an analog to digital converter and a computing device, said analog to digital converter operably associated with said current transformer to convey digital signals corresponding to current measured by said transformer to said computing device, said computing device being operably associated with said electrosurgical generator and constituting means to recognize the power setting of said generator, to recall the relationship of current to impedance characteristic of said generator at said power setting, to determine the load impedance of said circuit according to said measured current and said relationship of current to impedance, and to calculate from said load impedance the power delivered through said circuit to said target.

6. The apparatus of claim 5 wherein said current transformer continuously measures said current and said computing device continuously determines said impedance and delivered power during operation of said generator, and said computing device continuously integrates said delivered power over time during said operation and thereby calculates the total energy delivered to said target.

7. The apparatus of claim 6 wherein said computing device is further programmed with a limit value for the accumulated total dispersed energy, said apparatus further including switch means operably connected to computing device and said electrosurgical generator and responsive to said computing device for deactivation of said electrosurgical generator when said total delivered energy reaches said limit value.

8. The apparatus of claim 6 further including display means connected to said computing device for displaying said total delivered energy.

* * * * *